United States Patent [19]

Bailey

[11] 4,406,621

[45] Sep. 27, 1983

[54] COUPLING ENSEMBLE FOR DENTAL HANDPIECE

[75] Inventor: Ronald L. Bailey, St. Charles, Mo.

[73] Assignee: Young Dental Manufacturing Company, Inc., St. Louis, Mo.

[21] Appl. No.: 259,987

[22] Filed: May 4, 1981

[51] Int. Cl.³ .............................................. A61C 1/08
[52] U.S. Cl. .................................... 433/126; 433/133
[58] Field of Search ............... 433/126, 105, 114, 125, 433/130, 133

[56] References Cited

U.S. PATENT DOCUMENTS

| | | | |
|---|---|---|---|
| 1,984,663 | 12/1934 | Totham | 433/126 |
| 2,010,421 | 8/1935 | Terry | 433/126 |
| 2,448,758 | 9/1948 | Angell | 433/114 |
| 2,813,337 | 11/1957 | Uhler | 433/133 |
| 3,631,597 | 1/1972 | Lieb et al. | 433/126 |
| 4,245,985 | 1/1981 | Eibofner et al. | 433/126 |
| 4,278,429 | 7/1981 | Straihammer et al. | 433/105 |

FOREIGN PATENT DOCUMENTS

| | | | |
|---|---|---|---|
| 585898 | 10/1933 | Fed. Rep. of Germany | 433/126 |
| 599591 | 7/1934 | Fed. Rep. of Germany | 433/126 |
| 622765 | 12/1935 | Fed. Rep. of Germany | 433/126 |

Primary Examiner—John J. Wilson
Attorney, Agent, or Firm—Rogers, Eilers & Howell

[57] ABSTRACT

A dental handpiece having a head mounted to a shoulder has a coupling ensemble formed of two coupling assemblies. The first coupling assembly is mounted within the shoulder and comprises a gear mounted to a shaft with the shaft extending into a coupling hand. A second like coupling assembly has a bevel gear with a shaft extending therefrom into a coupling hand. The second assembly is mounted within a throat sleeve, which is mounted within the neck of the head. Each coupling hand has a pair of tongues, with slots formed between the side walls of the tongues, to allow the coupling hands to drivingly lock together. The tongues are shaped so that as they are moved into contact with each other, they are directed to have their side walls interlock with one another. The tongues can have anterior slanted walls extending into a point, to facilitate such directing of the tongues into interlocking position. The coupling ensemble thus allows the head to be dismounted from the shoulder so that another head with a different dental tool can be mounted to the shoulder. The first coupling assembly is located within the shoulder, so that when the second coupling assembly and the head are dismounted from the shoulder, the first coupling assembly is contained within the walls of the shoulder so that other objects will not come into engagement with it during rotation.

7 Claims, 4 Drawing Figures

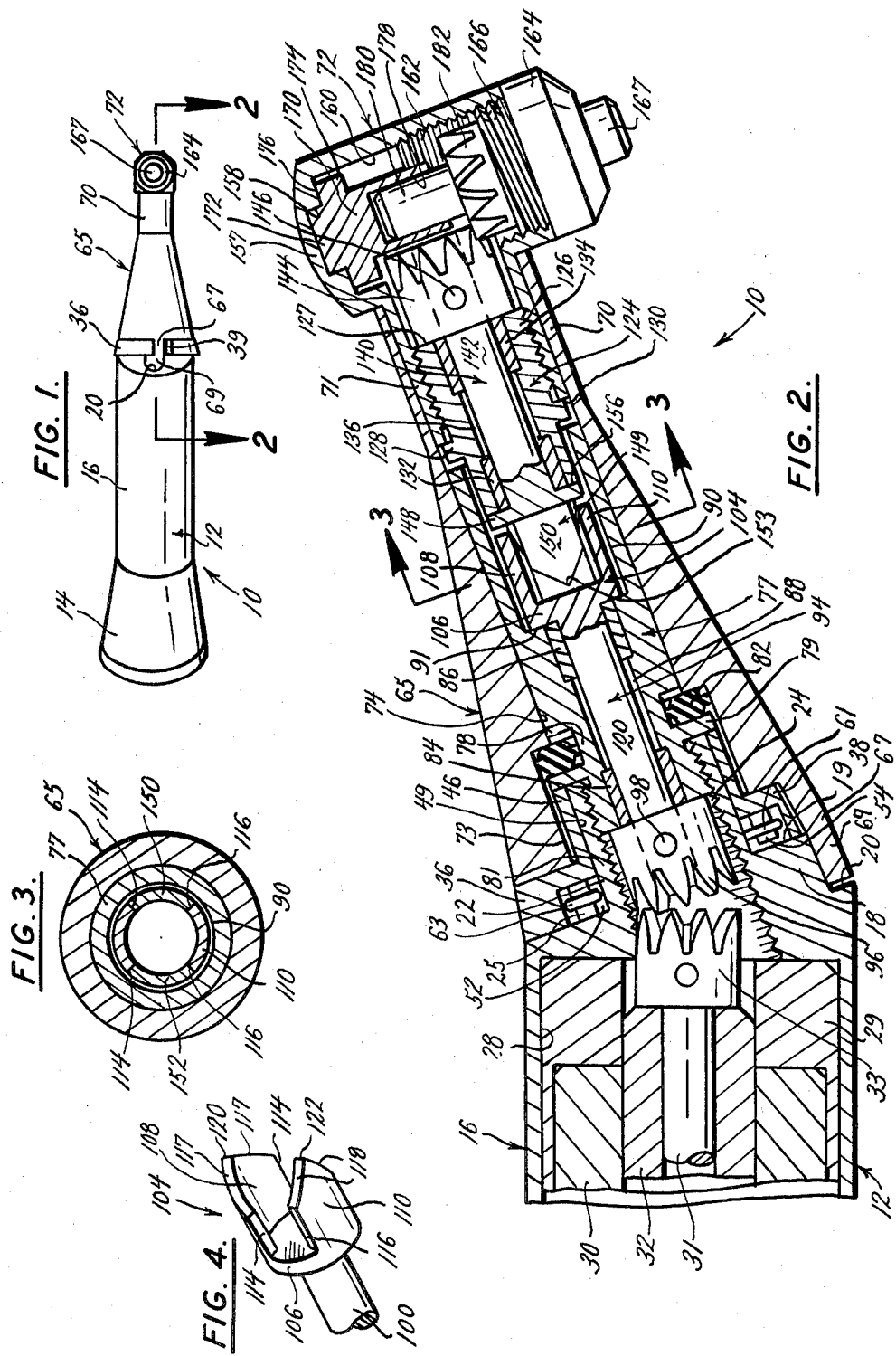

COUPLING ENSEMBLE FOR DENTAL HANDPIECE

BACKGROUND AND SUMMARY OF THE INVENTION

The present invention relates to dental handpiece coupling assemblies for drivingly connecting gears so as to rotate a dental tool in a dental head. It is desirable to have a dental handpiece which allows interchange of different dental tools according to the type of dental work necessary. One way to change dental tools is to simply remove the tool from the dental head and replace it with another desired tool. However, the small size of dental tools makes them difficult to handle. It is therefore desirable to interchange one dental head with another, so that the larger heads can be disconnected and re-connected to the handpiece, rather than having to handle the smaller individual tools themselves.

When two new gears are initially mated in a dental handpiece, they can be aligned so as to mesh properly for driving rotation. After a period of time, those first and second mating gears become worn and mishapened through use, so that their shape is somewhat distorted from their original shape. The alignment of the two gears with their surrounding elements can also be altered during use. Because the distortion and misalignment of the two gears occurs while they are mated, the distortions and misalignment are mirrored in the two gears, so that they remain in proper mesh and alignment with each other for driving engagement.

Thus, when one of these first or second mated gears is replaced by a third gear, the third gear may not mesh well with, or be aligned with, the other mating gear, because of the distortion that has been created between the two gears during their operation. This is true although the three gears were probably nearly identical after they were manufactured and before they were used. Therefore, it is desirable to have an interchange system whereby there is no substitution of either the driven gear or drive gear.

Another problem with meshing and unmeshing gears is that if the drive gear remains running when the driven gear is brought into mesh with it, the gear teeth may tear into each other and ruin the gears.

The present invention alleviates such problems. It provides a first coupling assembly mounted within the shoulder sleeve of a dental handpiece, so that it rotates therein. The first coupling assembly comprises a gear such as a bevel gear, which is driven by another gear that is driven from the power source. The first coupling assembly has a drive shaft extending from its gear into a coupling hand. In the preferred embodiment, the coupling hand comprises a pair of tongues mounted opposite one another with slots formed between the tongues.

The invention further comprises a second coupling assembly which can be similar to the first. The second assembly has a hand having a pair of tongues with slots formed therebetween. The second coupling assembly likewise has a drive shaft extending from its hand to connection with a gear. The second assembly can be mounted to the dental head by a throat sleeve so that the second assembly's gear is drivingly connected to a driven gear mounted within the head for purposes of driving a dental tool. The coupling assemblies thus allow the head to be attached and detached from the shoulder. In the preferred embodiment, the tongues of the first assembly fit in the slots between the tongues of the first coupling assembly, so that straight side walls of the tongues of both coupling assemblies fit flush with each other for driving connection.

In the preferred embodiment the tongues have anterior ends shaped to guide the tongues into driving engagement as they are moved towards one another. These ends can be slanted to come to a point. When the head is mounted to the shoulder, and the tongues of the second coupling assembly are moved towards the tongues of the first coupling assembly, the slanted ends engage and direct the tongues towards the slots formed between the side walls of the tongues.

Thus, the head with its second coupling assembly can be pulled away from the shoulder sleeve with its first coupling assembly to disengage the coupling assemblies. Another like head with a different dental tool mounted thereto, can then be substituted for the first head, and have its corresponding second coupling assembly moved back into the shoulder sleeve bore until the hand of the second coupling assembly interlocks with the hand of the first coupling assembly for driving engagement.

With the present invention there is thus provided a coupling assembly arrangement whereby mated gears remain with their mated gears during interchange of components. There is thus elimination of the situation where a gear is caused to mate with a foreign gear resulting in improper meshing and misalignment of the gears. This reduces the opportunity for malfunctioning. Thus, the special distortions and alignment of the gears formed as a result of their operation are not caused to be suddenly interacted with a foreign non-conforming gear shape.

Because the gears are not directly involved in the coupling change, during the installation and disconnection there is no moving of gear teeth into mesh or out of mesh, even if the installation or disconnection is performed while the dental tool is being operated. This eliminates the possibility of the gears tearing into each other during such installation and disconnection.

A further feature is that the first assembly can be mounted entirely within the walls of the shoulder so as to be recessed therein. There is thus no problem with snagging occurring if the dental power motor is allowed to run during the interchange process. The invention also provides bearing sleeves which properly mount the coupling assemblies for their operation.

DESCRIPTION OF THE DRAWINGS

FIG. 1 is a bottom plan view of the dental handpiece showing the head mounted to the shoulder and the shoulder locked to the handle;

FIG. 2 is a section of the handpiece taken on the line 2—2 of FIG. 1;

FIG. 3 is a section on the line 3—3 of FIG. 2, showing the tongues of the coupling assemblies interlocked with each other for driving engagement; and FIG. 4 is an orthogonal projection of a hand and shaft of of the first coupling assembly.

DESCRIPTION OF THE PREFERRED EMBODIMENT

The drawings show a handpiece 10 having a handle sleeve 12 that has a tapered section 14 which extends into a cylindrical trunk section 16. The tapered section 14 can be secured to another section, not shown. At its inner end handle 12 bends from trunk 16 into a short slanted end section 18 having a flat end surface 19. The exterior surface of section 18 has a U-shaped notch 20 for receiving a hook lug to be described. Projecting from end surface 19 is a unitary cylindrical sleeve 22 with a threaded bore 24. A pin 25 is press fit tightly within a cylindrical bore that extends into the end surface 19.

Handle 12 has an enlarged cylindrical bore 28 which receives a sleeve bearing 29. Another sleeve bearing 30 fits within a bore in sleeve bearing 29. A drive shaft 31 extends through a bore in a sleeve bearing handle 12 and is mounted to a bevel gear 33 by a pin.

Mounted for rotation relative to handle 12 is a lock ring 36. Ring 36 has an annular section 38 whose flat outer end fits flush against the flat end surface 19.

The outer surface of annular section 38 has a slot 39 which can be aligned with U-notch 20 when ring 36 is in the unlocked position.

Extending inwardly from annular section 38 is a unitary cylindrical sleeve 46 which has a cylindrical bore 49. Bore 49 telescopically receives sleeve 22. The ring annular section 38 has a cylindrical recess 52 so that an annular cavity is formed between ring 36 and sleeve 22.

Annular section 38 has a small cylindrical bore which tightly receives a pin 54. On the side of lock ring 36 opposite pin 54, is formed a small aperture (not shown) which receives the inner end of pin 25 so that pin 25 serves as a stop.

A helical spring (not fully shown) has hooked ends 61 and 63 which fit about pins 54 and 25, respectively, so that the spring is mounted to curve within ring recess 52 between sleeve 22 and annular section 38. Spring acts to bias ring 36 relative to handle 12. The stop pin 25 rests against the end of its ring aperture to prevent further rotation.

To the inside of handle 12 is a tapered shoulder sleeve 65. The outer end of shoulder 65 has a tongue 67 having a locking lug 69 formed at its outer end that is sized to be received within the handle notch 20. The tongue 67 is of less width than the width of ring notch 39, so that the spring can bias the ring 36 to cause part of the ring to block handle notch 20, thus capturing the lug 69 within notch 20 to lock the shoulder 65 to the handle 12. The ring 36 can be rotated to align slot 39 with handle notch 20, which allows lug 69 to pass through slot 39 to allow disengagement of shoulder 65 from handle 12.

Shoulder 65 is of a generally conical shape, and has a cylindrical collar sleeve 70 which snugly receives within it the internally threaded cylindrical neck sleeve 71 of cross head 72. Shoulder 65 has, at its outer end, a cylindrical bore 73 which receives telescopically ring sleeve 46. Bore 73 extends inwardly into a smaller cylindrical bore 74, which slidingly receives an intermediate cylindrical bearing sleeve 77. At its outer end, intermediate sleeve 77 has a cylindrical neck 78 that extends outwardly into a cylindrical flange 79, which flange is received within bore 73. Bearing 77 has, extending outwardly from flange 79, a threaded portion which screws into the threaded end 81 of handle sleeve 22 so that the flat outer end of flange 79 mounts flush against the flat inner surfaces of handle sleeve 22 and ring sleeve 46, to hold the lock ring in the position shown in FIG. 2.

An annular rubber washer 82 is mounted about bearing neck 78 adjacent the inner end of circular flange 79 so as to fit within bore 73.

The ring 36 fits with handle 12 and shoulder 65 so that the exterior surface of ring 36 is approximately flush with the adjacent exterior surfaces of handle 12 and shoulder 65.

Within conforming bores of intermediate sleeve 77 are a pair of cylindrical sleeve bearings 84 and 86, spaced apart by a bore 88 of smaller size. Inward from bearing 86, sleeve 77 has a larger bore 90 with a shoulder 91 formed to extend even with the inner end of sleeve 86. A first coupling assembly 94 comprises a bevel gear 96 mounted by a pin 98 to a cylindrical shaft 100 so that gear 96 meshes with gear 33, and the flat inner end of gear 96 rests flush against the flat outer ends of sleeve section 81 and sleeve 84. Shaft 100 is telescopically and rotatably received within the bores of sleeves 84 and 86. At the inner end of shaft 100 is a unitary coupling hand 104 comprising a circular disc section 106 from which extend two identical tongues 108 and 110 mounted directly opposite each other. Tongues 108 and 110 are both of semi-cylindrical cross section, with straight flat side walls such as walls 114 and 116 for tongues 108 and 110 respectively, shown in FIG. 4. From the inner ends of straight walls 114 and 116, the tongues extend into slanted walls 117 and 118 which slant and curve into pointed ends 120 and 122. As shown in FIG. 2, coupling hand 104 fits well within sleeve bore 90.

Inwardly from sleeve 77 is a throat sleeve 124 which has an externally threaded inner section 126, with a flat end 127, which screws into the internal threads of neck 71. The circular flange 128 of the throat abuts the outer end 130 of neck 71. Within conforming bores of throat 124 are a pair of sleeve bearings 132 and 134 (of the same size as sleeves 84 and 86) spaced apart by a throat bore 136 of smaller size.

A second coupling assembly 140 is of similar components, but of shorter length than coupling assembly 94. Assembly 140 comprises a shaft 142 connected to a bevel gear 144 by a pin 146 for rotation therewith. From there, shaft 142 extends through the bores in sleeves 134 and 132, into a hand 149 comprising a circular disc 148, from which extend a pair of identical tongues 150 and 152 (tongue 150 being shown in FIG. 2) of the same shape as tongues 108 and 110. Each tongue has a pair of straight side walls corresponding to walls 114 and 116 of tongues 108 and 110, and a pair of slanted walls corresponding to slanted walls 117 and 118 of tongues 108 and 110, which slant and curve into pointed ends, such as end 153 shown for tongue 150 in FIG. 2. The tongues of each hand interlock with one another so that the straight side walls of tongues 108 and 110 are aligned with, and fit flat against, the straight side walls of tongues 150 and 152, as shown in FIG. 3. The inner side of disc 148 rests flush against the outer end of sleeve 132 and outer end 156 of throat 124.

The positive interlock of the tongues is such that rotation of gear 96 rotates hand 104 which in turn rotates hand 149 and gear 144. The shafts 100 and 142 are axially guided during rotation by their bearings 84 and 86, 132 and 134 respectively. In the interlocked position, hand 104 has its pointed ends 120 and 122 of respective tongues 108 and 110 spaced from the disc 148 of the opposite hand 149, while the same is true of the pointed ends of tongues 150 and 152 which are spaced from the disc 106 of hand 104.

Intermediate sleeve shoulder 91 and an end of bearing sleeve 86 provide thrust bearing surface for the outer side of disc 106 for smooth rotation. The restraint provided by gear 96 against intermediate sleeve section 81 and sleeve bearing 84 prevents further movement of hand 104 towards head 72. Likewise throat sleeve end 156 and an end of sleeve bearing 132 provide thrust bearing surface for the inner side of disc 148 so that disc 148 rotates smoothly thereagainst. The restraint provided by gear 144 against intermediate sleeve end 127 and bearing sleeve 134 prevent further movement of hand 149 away from head 72.

Continuing with discussion of the head 72, the neck sleeve 71 is telescopically snugly received within collar 70 so that the neck 71 can be pulled out of collar 70 by grasping head 72 by the fingers and rotating the neck while pulling the neck out of the collar to gradually disconnect the neck from the collar. The head 72 has a closed end 157 with an upper cylindrical bore 158 which extends downward into a larger main bore 160, which has a lower internally threaded section 162.

A cap 164 has an upper externally threaded extension 166 which screws into threaded section 162, and has a lower cylindrical extension 167. Within the head is a bearing sleeve 170 having an upper cylindrical end 172 that fits within head bore 158 for rotation therein, and having an enlarged cylindrical section 174 whose upper end rests flush against the shoulder surface 176 located between bores 158 and 160, for rotation thereagainst.

Bearing sleeve 170 has a lower cylindrical bore 178 which rotatably receives a cylindrical shaft 180 that is connected to a driven gear 182. Gear 182 meshes with gear 144. Depending downwardly from gear 182 through a bore in cap 164, and its sections 166 and 167, is a shaft (not shown) which is internally threaded for the mounting of a dental tool such as a cleaning cup.

Thus there is a drive train from shaft 31 through gear 33, through coupling assemblies 94 and 140, to rotate gear 182.

OPERATION

Our description of the operation commences with the handpiece positioned as shown in FIGS. 1, 2 and 3. In this position rotation of shaft 31 is transmitted through the drive train described to drive gear 182 in head 72 to thus drive the dental tool connected to gear 182.

The changing of dental tools can be performed by changing dental head assemblies, rather than detaching the tool from the head. The head 72 can be removed from the shoulder 65 by grasping the head 72 with the fingers and pulling it away from shoulder 65, which also causes the throat sleeve 124 to be pulled away from shoulder 65. Since coupling assembly 140 is mounted to the throat sleeve 124, the coupling assembly 140 is also pulled away from the shoulder 65 as the head is removed. Pulling coupling assembly 140 away pulls the hand 149 and its tongues 150 and 152 out of engagement with hand 104 and its tongues 108 and 110. The head 72 is continued to be pulled outwardly from collar 70 until the hand 149 is completely removed from within the collar 70.

The above discussed disengagement of hands 104 and 149 can be performed while both hands 104 and 149 are being rotatably driven, without fear of misalignment or destructive interengagement of the hands. This ease in disengagement is facilitated by the structure of the tongues, including their slanted and curved walls such as walls 117 and 118 for tongues 108 and 110. In analyzing the removal of the two hands 104 and 149 from one another, the tongues are initially interlocked so that their straight side walls, such as the straight walls 114 and 116 for tongues 108 and 110, are matched with the corresponding side walls of tongues 150 and 153. As the hands 104 and 149 are moved apart, the straight side walls of the tongues become disengaged from one another and the slanted walls of the tongues then slide against each other until the tongues are pulled apart so that the slanted side walls are disengaged. In this way there is no abrupt shock of impact of the tongues against each other as they are removed, and the slanted walls also provide for a larger area for force distribution.

When the coupling assembly 140 is withdrawn from collar 70, the coupling assembly 94 can continue to be rotated without fear of its snagging or tearing another object. This is because the hand 104 is contained entirely within bore 90 of the intermediate sleeve 77, which is well within the confines of shoulder 65. The only way in which hand 104 can snag against another object is if the object is stuffed through collar 70 into engagement with hand 104. Thus, it is not necessary to turn off the motor during the disengagement of the coupling assemblies.

Once the coupling assembly 140 is disengaged from the driving coupling assembly 94, the assembly 140 is no longer rotated and can thus be safely removed from collar 70.

After the head 72 is disengaged, another like head with a different dental tool mounted thereto can be mounted to shoulder 65. Preferably this mounting is performed with coupling assembly 94 stationary within the shoulder 65. This mounting is performed by grasping the replacement head 72 with the fingers and inserting its neck 71 within collar 70 and sliding the neck into the collar to thus move hand 149 towards hand 104. The hands are moved towards each other until their slanted side walls engage with each other, and after such engagement the slanted walls slide against each other to direct the tongues so that the tongues of one hand fit within the straight side walls of the other hand, as shown in FIGS. 2 and 3.

The fitting of the head 72 to the shoulder 65 can also be performed while the coupling assembly 94 is rotated. In this case the slanted walls of the tongues interact as described to guide the tongues so that their straight side walls fit flat against each other as shown in FIGS. 2 and 3.

With the hands thus engaged, the coupling assemblies are connected so that rotation of gear 33 again drives gear 182 within the head.

Thus, heads having different dental tools mounted thereto can be attached and detached to and from shoulder 65 to provide a quick interchange of dental tools without having to individually mount and dismount the dental tool from the particular head.

Various changes and modifications may be made to applicant's invention as would be apparent to those skilled in the art. However, any of these changes and modifications are included in the teachings of applicant's disclosure and he intends that his invention be limited only by the scope of the claims appended hereto.

I claim:

1. In a dental handpiece: a trunk section, a shoulder sleeve angularly extending from the trunk section; a power drive comprising a first drive shaft rotatably mounted in the trunk section; a second shaft rotatably mounted in the shoulder sleeve, and extending angularly out from the first drive shaft, a first angular coupling drive means having an element on each of said first and second shafts, the elements being interengaged to connect the two shafts for driving of the second shaft by the first; a head having a third shaft rotatably mounted therein, and a fourth driven shaft rotatably mounted in the head at an angle to the third shaft; second angular coupling drive means in the head having an element on each of said third and fourth shafts, the elements being interengaged to connect the third shaft to the fourth shaft for driving the fourth shaft by the third; the head having releasable connecting means with the sleeve by which the head is mounted on the sleeve by axial thrusting movement, with the second and third shafts in juxtaposition, and release coupling means between said second and third shafts respectively having first and second hand elements which have axially disposed interengaging elongated edges which are engageable and disengageable upon mounting and separation of the head by axial movements, for drivingly connecting and disconnecting the second and third shafts, the first and second driving means aforesaid being fixed axially on their respective shafts, means to restrain axial movement of the second shaft, and means to restrain axial movement of the third shaft upon connecting and disconnecting of the release coupling means.

2. The ensemble of claim 1 wherein the shoulder sleeve has a bore, and with the first hand element contained entirely within said shoulder bore.

3. The structure of claim 1 further comprising a first bearing sleeve mounted within the shoulder sleeve, and wherein the first coupling drive means comprises a first gear on the first shaft in the trunk section, and a second gear on the second shaft, the second gear being drivingly connected to the first coupling hand by the second shaft, the release coupling means comprising a first hand element on the second shaft and a second hand element on the third shaft, with the first bearing sleeve having a bore section of smaller diameter than the second gear and the first coupling hand, with the second shaft extending therethrough to mount the first coupling means to the first bearing sleeve so that axial movement of the first coupling means relative to the first sleeve is resisted.

4. The structure of claim 3 wherein the second coupling drive means comprises a third gear and a fourth gear, with the third shaft connecting the third gear to the second coupling hand for driving rotation.

5. The structure of claim 3 wherein the second coupling drive means further comprises a second collar sleeve mounted to the head, said second collar sleeve having a bore section of smaller diameter than the third gear and the second coupling hand, with the third shaft extending through said bore section to mount the third gear onto the head to resist axial movement relative thereto, so that when the head is removed from the shoulder, the second collar sleeve and the third shaft, the third gear and the second head remain mounted to the head.

6. In the handpiece of claim 1, the releasable connecting means between the head and shoulder sleeve comprising telescopic interfitting elements.

7. A coupling ensemble for a dental handpiece comprises:
(a) a head detachably mounted to a shoulder sleeve having a bore, a trunk section of a dental handpiece to which the shoulder is mounted, with a first sleeve having a bore mounted into the trunk so as to be contained within the back of the shoulder sleeve;
(b) a first coupling assembly mounted within the shoulder sleeve for rotation relative thereto, said coupling assembly comprising a first coupling hand, a first gear drivingly connected to the first coupling hand by a first shaft, with the first sleeve having a bore section of smaller diameter than the first gear and the first coupling hand, with the first shaft extending therethrough to mount the first coupling assembly to the first sleeve so that axial movement of the first coupling assembly relative to the first sleeve is resisted;
(c) a second sleeve having a bore, mounted to the head, and a second coupling assembly mounted within the second sleeve bore for rotation therewith, said second coupling assembly comprising a second coupling hand and a second gear with a second shaft connecting the second gear to the second coupling hand for driving rotation, said second sleeve bore section being of smaller diameter than the second gear and the second coupling hand, with the second shaft extending through said second sleeve bore to mount the second coupling assembly to the second sleeve to resist axial movement relative thereto, so that when the head is removed from the shoulder, the second sleeve and second coupling assembly remain mounted to the head; and
(d) the first coupling hand being shaped with first means for coupling, comprising a first pair of tongues, each tongue having a pair of side walls; and the second coupling hand being shaped with second means for coupling, comprising a second pair of tongues, each tongue having a pair of side walls, so that the first and second hands engage each other with the side walls of the first tongues in contact with the side walls of the second tongues to allow the first coupling assembly to drivingly rotate the second coupling assembly, wherein the tongues for the first hand are shaped at their anterior ends with means for directing the tongues of the second hand towards a position between the first hand tongues when the first and second hands are moved towards each other to contact each other, and so that the head can be pulled away from the shoulder to disconnect the head from the shoulder and disconnect the first coupling assembly from the second coupling assembly.

* * * * *